United States Patent
Kim et al.

(10) Patent No.: US 10,682,094 B2
(45) Date of Patent: Jun. 16, 2020

(54) WATCH TYPE TERMINAL

(71) Applicant: LG ELECTRONICS INC., Seoul (KR)

(72) Inventors: Dongwook Kim, Seoul (KR); Kiyoon Nam, Seoul (KR); Jeongjoong Kim, Seoul (KR); Heonjoong Lee, Seoul (KR)

(73) Assignee: LG ELECTRONICS INC., Seoul (KR)

( * ) Notice: Subject to any disclaimer, the term of this patent is extended or adjusted under 35 U.S.C. 154(b) by 0 days.

(21) Appl. No.: 16/464,210

(22) PCT Filed: Dec. 7, 2016

(86) PCT No.: PCT/KR2016/014279
§ 371 (c)(1),
(2) Date: May 24, 2019

(87) PCT Pub. No.: WO2018/105773
PCT Pub. Date: Jun. 14, 2018

(65) Prior Publication Data
US 2019/0388028 A1    Dec. 26, 2019

(51) Int. Cl.
*A61B 5/00*       (2006.01)
*A61B 5/024*      (2006.01)
(Continued)

(52) U.S. Cl.
CPC .............. *A61B 5/681* (2013.01); *A61B 5/024* (2013.01); *G04G 17/02* (2013.01); *H01Q 1/243* (2013.01); *H01Q 1/521* (2013.01)

(58) Field of Classification Search
CPC ......... G04G 17/02; H01Q 1/243; H01Q 1/521
See application file for complete search history.

(56) References Cited

U.S. PATENT DOCUMENTS

2016/0294427 A1    10/2016  Wojcik
2017/0133751 A1*   5/2017   Noh .................... G06K 7/10336

FOREIGN PATENT DOCUMENTS

KR     1020130010797        1/2013
KR       101458160          11/2014
(Continued)

OTHER PUBLICATIONS

PCT International Application No. PCT/KR2016/014279, Written Opinion of the International Searching Authority dated Jul. 26, 2017, 21 pages.

*Primary Examiner* — Nguyen T Vo
(74) *Attorney, Agent, or Firm* — Lee, Hong, Degerman, Kang & Waimey (57) ABSTRACT

A mobile terminal of the present invention comprises: a front case having a display unit disposed on a front surface thereof; a rear case coupled to the front case at the rear of the front case to form an inner space; a main board located in the inner space and comprising mounted components coupled to a surface thereof; a shielding sheet laminated on a back surface of the main board; and a wireless charging coil located in the inner space, wherein the shielding sheet has empty spaces at positions where the wireless charging coil and the mounted components overlap with each other. Accordingly, the main body of the mobile terminal can be prevented from becoming thick by forming the shielding sheet for enhancing the performance of the wireless charging coil in a shape that does not overlap with the wireless charging coil and the mounted components at the same time.

10 Claims, 9 Drawing Sheets

(51) Int. Cl.
 G04G 17/02 (2006.01)
 H01Q 1/24 (2006.01)
 H01Q 1/52 (2006.01)

(56) References Cited

FOREIGN PATENT DOCUMENTS

KR 101570425 11/2015
KR 1020160101627 8/2016

* cited by examiner

WATCH TYPE TERMINAL

CROSS-REFERENCE TO RELATED APPLICATIONS

This application is the National Stage filing under 35 U.S.C. 371 of International Application No. PCT/KR2016/014279, filed on Dec. 7, 2016, the contents of which are all hereby incorporated by reference herein in its entirety.

FIELD

Embodiments of the present disclosure relate to a watch type terminal having an analog clock hands.

BACKGROUND

Terminals may be generally classified as mobile/portable terminals or stationary terminals according to their mobility. Mobile terminals may also be classified as handheld terminals or vehicle mounted terminals according to whether or not a user can directly carry the terminal.

Mobile terminals have become increasingly more functional. Examples of such functions include data and voice communications, capturing images and video via a camera, recording audio, playing music files via a speaker system, and displaying images and video on a display. Some mobile terminals include additional functionality which supports game playing, while other terminals are configured as multimedia players. More recently, mobile terminals have been configured to receive broadcast and multicast signals which permit viewing of content such as videos and television programs.

As such functions become more diversified, the watch type terminal can support more complicated functions such as capturing images or video, reproducing music or video files, playing games, receiving broadcast signals, and the like. By comprehensively and collectively implementing such functions, the watch type terminal may be embodied in the form of a multimedia player or device.

As types of such mobile terminals are diversified, there are released hand-carry type mobile terminals and wearable type terminals. In this instance, an exterior design is so important in such a wearable type terminal. When a display unit of the wearable type terminal is deactivated, a clockface or alphabetical keypad becomes dark and the exterior design then becomes deteriorated disadvantageously. In addition, a battery capacity becomes a problem when a display unit is always activated.

Furthermore, the wearable terminal has a problem of an insufficient space for loading diverse components, because it has a limited size. Especially, there is mutual interference between an antenna using an electromagnetic wave signal and a wireless charging coil so that it can be difficult to arrange them.

DETAILED DESCRIPTION OF THE INVENTION

Technical Problem

To overcome the disadvantages, an object of the present invention is to address the above-noted and other problems and provide a watch type terminal that uses a metal structure as antenna.

Technical Solution

To achieve these objects and other advantages and in accordance with the purpose of the embodiments, as embodied and broadly described herein, a watch type terminal comprises a front case having a front surface in which a display unit is arranged; a rear case coupled to the front case from a rear area of the front case and configured to form an internal space; a main board provided in the internal space and comprising the components loaded in a surface; a shielding sheet disposed on a rear surface of the main board; and a wireless charging coil provided in the internal space, wherein the shielding sheet has an omitted area corresponding to an overlapped area between the wireless charging coil and the loaded components.

The loaded components may comprise at least one of a shield can configured to cover a main chip or a connector connected with the other components.

The watch type terminal may further comprise a rear surface component exposed via an opening formed in a rear surface of the rear case, wherein the shielding sheet has an omitted area corresponding to the rear surface components.

The rear component comprises at least one of a heartrate sensor or an USIM loading unit.

The watch type terminal may further comprise an auxiliary board disposed in a rear surface of the main board and having the heartrate sensor loaded therein.

The watch type terminal may further comprise a rib projected from the rear case towards the internal space, wherein the shielding sheet has an omitted area corresponding to the rib.

The watch type terminal may further comprise a magnet loaded in the internal space, wherein the shielding sheet has an omitted area corresponding to the magnet.

The wireless charging coil may be formed in a ring shape having an empty central area, and the shielding sheet may comprise a first shielding portion arranged in the empty central area of the wireless charging coil.

The watch type terminal may further comprise a second shielding portion overlapped with the wireless charging coil and located between the wireless charging coil and the main board.

The second shielding may be thinner than the first shielding portion.

The rear case may comprise a first rear case coupled to the front case; a second case detachably provided in the first rear case; and a projection layer configured to cover a predetermined area of the exposed area provided in the shielding sheet when the second rear case is separated.

Advantageous Effects

Accordingly, the embodiments have following advantageous effects. According to the embodiments of the present disclosure, the watch type terminal has the shielding sheet provided to improve the function of a wireless charging coil, the shielding sheet that is formed in a predetermined shape not to be overlapped with the wireless charging coil and the loaded components. Accordingly, the main case may be prevented from being thick.

Further scope of applicability of the present invention will become apparent from the detailed description given hereinafter. However, it should be understood that the detailed description and specific examples, while indicating preferred embodiments of the invention, are given by illustration only, since various changes and modifications within the spirit and scope of the invention will become apparent to those skilled in the art from this detailed description.

DESCRIPTION OF SPECIFIC EMBODIMENTS

Description will now be given in detail according to exemplary embodiments disclosed herein, with reference to the accompanying drawings. For the sake of brief description with reference to the drawings, the same or equivalent components may be provided with the same reference numbers, and description thereof will not be repeated. In general, a suffix such as "module" and "unit" may be used to refer to elements or components. Use of such a suffix herein is merely intended to facilitate description of the specification, and the suffix itself is not intended to give any special meaning or function. In the present disclosure, that which is well-known to one of ordinary skill in the relevant art has generally been omitted for the sake of brevity. The accompanying drawings are used to help easily understand various technical features and it should be understood that the embodiments presented herein are not limited by the accompanying drawings. As such, the present disclosure should be construed to extend to any alterations, equivalents and substitutes in addition to those which are particularly set out in the accompanying drawings.

It will be understood that although the terms first, second, etc. may be used herein to describe various elements, these elements should not be limited by these terms. These terms are generally only used to distinguish one element from another.

It will be understood that when an element is referred to as being "connected with" another element, the element can be directly connected with the other element or intervening elements may also be present. In contrast, when an element is referred to as being "directly connected with" another element, there are no intervening elements present.

A singular representation may include a plural representation unless it represents a definitely different meaning from the context.

Terms such as "include" or "has" are used herein and should be understood that they are intended to indicate an existence of several components, functions or steps, disclosed in the specification, and it is also understood that greater or fewer components, functions, or steps may likewise be utilized.

The mobile terminal may be expanded to a wearable device that is wearable on a user's body part over a hand-carry type that is usually carried by a user in the hand. Examples of such a wearable device include a smart watch, a smart glass, a head mounted display (HMD) and the like. Hereinafter, examples of the mobile terminal expanded as the wearable device will be described.

Figure 1:
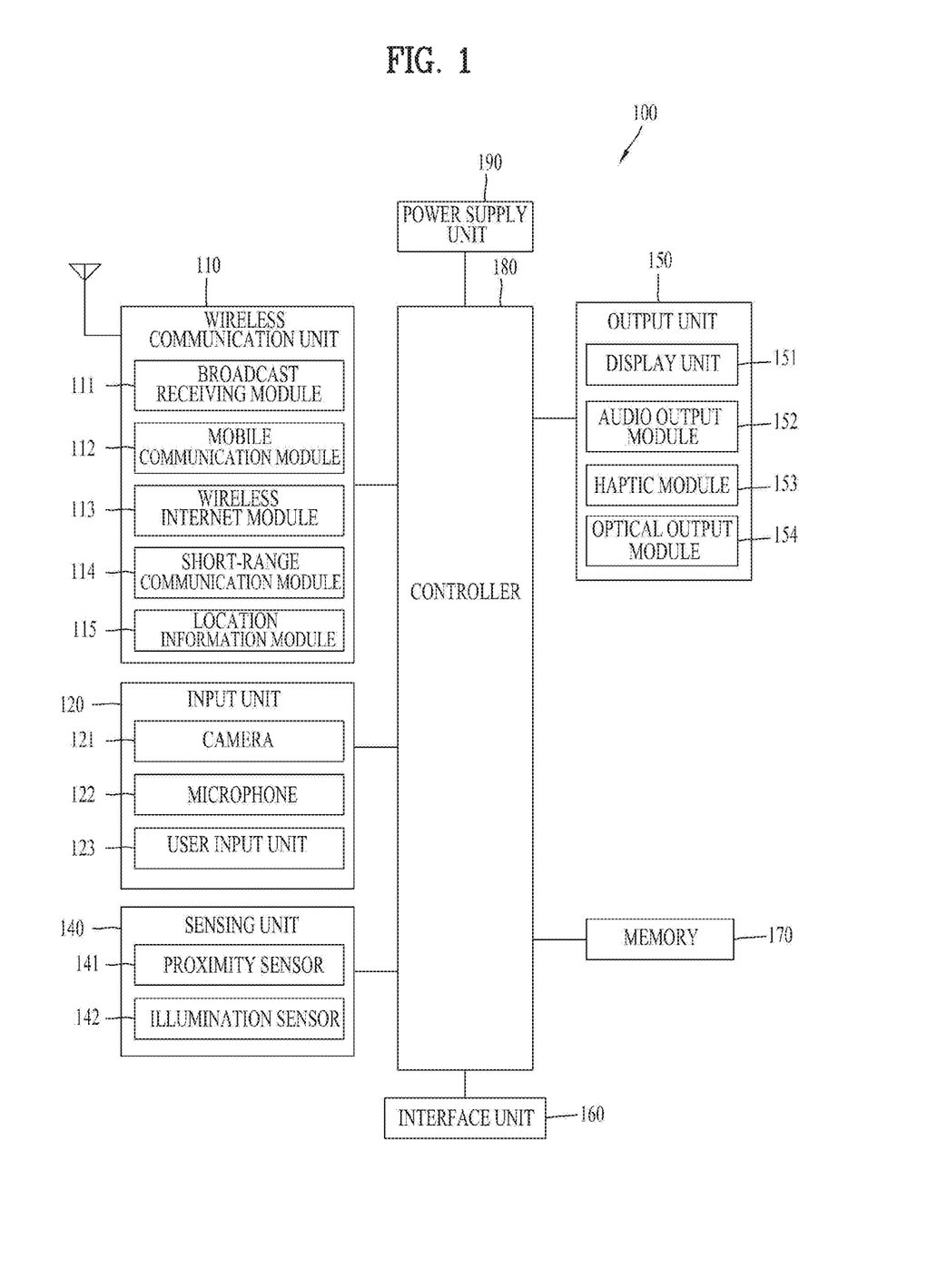
FIG. 1 is a block diagram of a mobile terminal in accordance with the present disclosure.

Reference is now made to FIG. 1, where FIG. 1 is a block diagram of a mobile terminal in accordance with the present disclosure.

The mobile terminal 100 is shown having components such as a wireless communication unit 110, an input unit 120, a sensing unit 140, an output unit 150, an interface unit 160, a memory 170, a controller 180, and a power supply unit 190. It is understood that implementing all of the illustrated components in FIG. 1 is not a requirement, and that greater or fewer components may alternatively be implemented.

More specifically, the wireless communication unit 110 typically includes one or more modules which permit communications such as wireless communications between the mobile terminal 100 and a wireless communication system, communications between the mobile terminal 100 and another mobile terminal, communications between the mobile terminal 100 and an external server. Further, the wireless communication unit 110 typically includes one or more modules which connect the mobile terminal 100 to one or more networks.

To facilitate such communications, the wireless communication unit 110 includes one or more of a broadcast receiving module 111, a mobile communication module 112, a wireless Internet module 113, a short-range communication module 114, and a location information module 115.

The input unit 120 includes a camera 121 for obtaining images or video, a microphone 122, which is one type of audio input device for inputting an audio signal, and a user input unit 123 (for example, a touch key, a push key, a mechanical key, a soft key, and the like) for allowing a user to input information. Data (for example, audio, video, image, and the like) is obtained by the input unit 120 and may be analyzed and processed by controller 180 according to device parameters, user commands, and combinations thereof.

The sensing unit 140 is typically implemented using one or more sensors configured to sense internal information of the mobile terminal, the surrounding environment of the mobile terminal, user information, and the like. For example, the sensing unit 140 may alternatively or additionally include other types of sensors or devices, such as a proximity sensor 141 and an illumination sensor 142, a touch sensor, an acceleration sensor, a magnetic sensor, a G-sensor, a gyroscope sensor, a motion sensor, an RGB sensor, an infrared (IR) sensor, a finger scan sensor, a ultrasonic sensor, an optical sensor (for example, camera 121), a microphone 122, a battery gauge, an environment sensor (for example, a barometer, a hygrometer, a thermometer, a radiation detection sensor, a thermal sensor, and a gas sensor, among others), and a chemical sensor (for example, an electronic nose, a health care sensor, a biometric sensor, and the like), to name a few. The mobile terminal 100 may be configured to utilize information obtained from sensing unit 140, and in particular, information obtained from one or more sensors of the sensing unit 140, and combinations thereof.

The output unit 150 is typically configured to output various types of information, such as audio, video, tactile output, and the like. The output unit 150 is shown having a display unit 151, an audio output module 152, a haptic module 153, and an optical output module 154. The display unit 151 may have an inter-layered structure or an integrated structure with a touch sensor in order to facilitate a touch screen. The touch screen may provide an output interface between the mobile terminal 100 and a user, as well as function as the user input unit 123 which provides an input interface between the mobile terminal 100 and the user.

The interface unit 160 serves as an interface with various types of external devices that can be coupled to the mobile terminal 100. The interface unit 160, for example, may include any of wired or wireless ports, external power supply ports, wired or wireless data ports, memory card ports, ports for connecting a device having an identification module, audio input/output (I/O) ports, video I/O ports, earphone ports, and the like. In some cases, the mobile terminal 100 may perform assorted control functions associated with a connected external device, in response to the external device being connected to the interface unit 160.

The memory 170 is typically implemented to store data to support various functions or features of the mobile terminal 100. For instance, the memory 170 may be configured to store application programs executed in the mobile terminal 100, data or instructions for operations of the mobile terminal 100, and the like. Some of these application programs may be downloaded from an external server via wireless communication. Other application programs may be installed within the mobile terminal 100 at time of manufacturing or shipping, which is typically the case for basic functions of the mobile terminal 100 (for example, receiving a call, placing a call, receiving a message, sending a message, and the like). It is common for application programs to be stored in the memory 170, installed in the mobile terminal 100, and executed by the controller 180 to perform an operation (or function) for the mobile terminal 100.

The controller 180 typically functions to control overall operation of the mobile terminal 100, in addition to the operations associated with the application programs. The controller 180 may provide or process information or functions appropriate for a user by processing signals, data, information and the like, which are input or output, or activating application programs stored in the memory 170.

To drive the application programs stored in the memory 170, the controller 180 may be implemented to control a predetermined number of the components mentioned above in reference with FIG. 1. Moreover, the controller 180 may be implemented to combinedly operate two or more of the components provided in the mobile terminal 100 to drive the application programs.

The power supply unit 190 can be configured to receive external power or provide internal power in order to supply appropriate power required for operating elements and components included in the mobile terminal 100. The power supply unit 190 may include a battery, and the battery may be configured to be embedded in the terminal body, or configured to be detachable from the terminal body.

Some or more of the components may be operated cooperatively to embody an operation, control or a control method of the mobile terminal in accordance with embodiments of the present disclosure. Also, the operation, control or control method of the mobile terminal may be realized on the mobile terminal by driving of one or more application problems stored in the memory 170.

Figure 2:
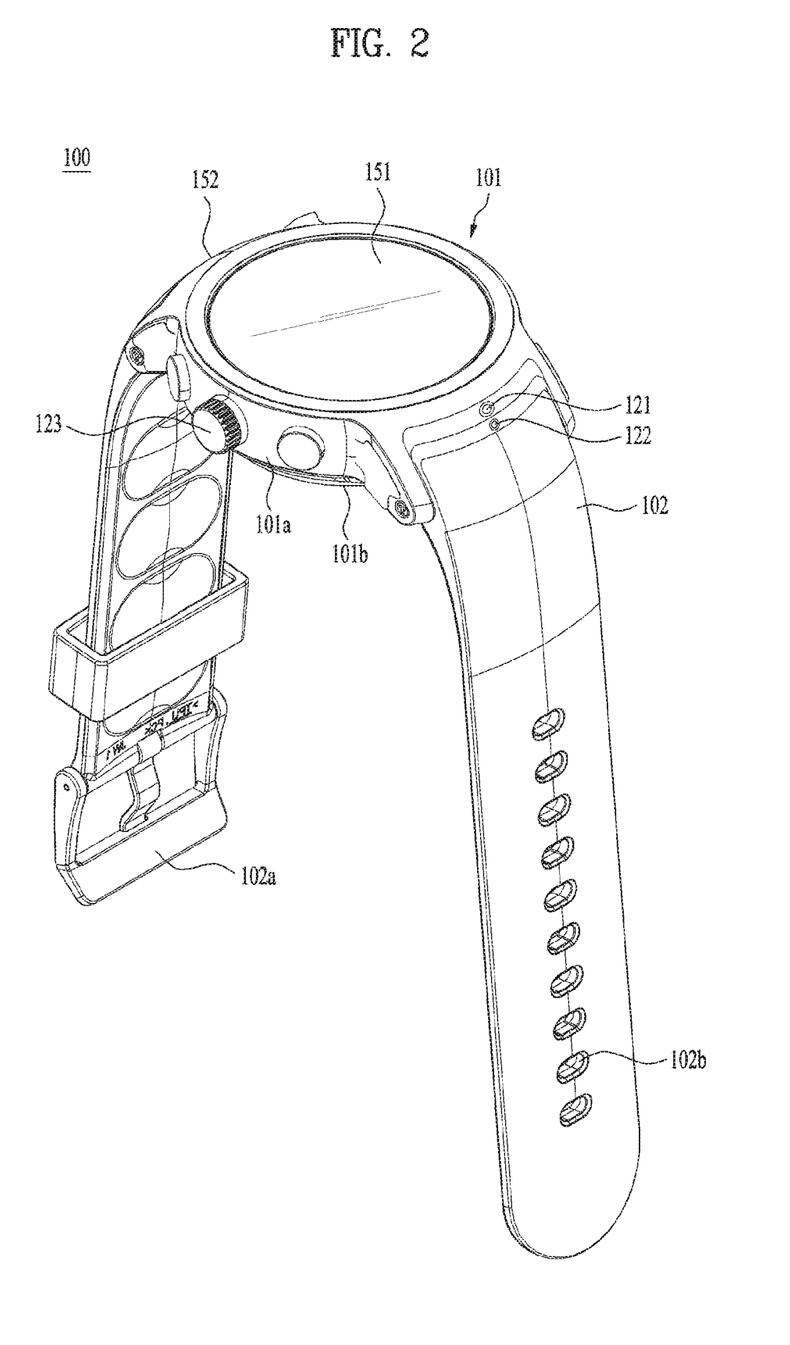
FIG. 2 is a perspective diagram of the watch type terminal.

FIG. 2 is a perspective diagram of the watch type mobile terminal 100. Referring to FIG. 2, the watch type mobile 100 includes a main body 101 having a display unit 151; and a band 102 connected with the body 101 and configured to be wearable on a user's wrist.

The body 101 includes a case 101a and 101b and defines an exterior design. As shown in the drawing, the case 101a and 101b may define an internal space that accommodates diverse electronic components including a main board 181 in which an electronic element for controlling the terminal is loaded, a camera 121 and an audio output unit 152.

The watch type terminal 100 is wireless-communicable and an antenna for such wireless-communication may be installed in the body 101. Meanwhile, the antenna may have an expanded function facilitated by using the case 101a and 101b. As one example, the case 101a and 101b including a conductive material may be electrically connected with the antenna to expand a ground area or a radiation area.

The case 101a and 101b may include a front case 101a arranged in a front surface; and a rear case 101b arranged in a rear surface. The front case 101a and the rear case 101b may partially form a lateral surface of the body or further include a side case.

The display unit 151 may be arranged on the front surface of the body 101 to output information. A touch sensor may be provided in the display unit 151 to be realized as a touch screen. As shown in the drawing, a window 151a of the display unit 151 may be coupled to the front case 101a configured as the front surface of the body 101 to form the front surface of the terminal body, together with the front case 101a.

In the body 101 may be provided an audio output unit 152, a camera 121, a microphone 122, a user input unit 123 and the like. When realized as the touch screen, the display unit 151 may function as the user input unit 123 and no additional key may be provided in the body 101.

The rear case 101b is a part that directly touches the user's body so that no heat has to be transferred to the body directly. Recently, a heartrate sensor or a temperature sensor may be provided in the area that directly contacts with the user's body and configured to collect information about the user's body.

The body may contact with the user's body and moisture such as sweat is likely to permeate into the body 101. A waterproof sealing 106, including 106a and 106b, made of an elastic material such as silicon for a waterproof function may be provided between the front case 101a and the rear case 101b.

The band 102 may be wearable on the user's wrist and configured to surround the wrist. The band 101 may be made of a flexible material to facilitate the wearing. Examples of the flexible material used for the band 102 may be made of leather, robber, silicon and a synthetic resin material. In addition, the band 102 may be detachably coupled to the body 101 and changeable as diverse types of bands according to the user's taste.

The band 102 may include a fastener 102a. The fastener 102a may be realized by a buckle, a hook structure that facilitates a snap-fit or Velcro. The fastener 102a may include an extendible section or material. In the drawing, the fastener 102a is realized as the buckle type. When the buckle type fastener 102a is provided, a hole 102b may be formed in the opposite band 102 to insert a securing pin of the buckle therein.

Figure 3:
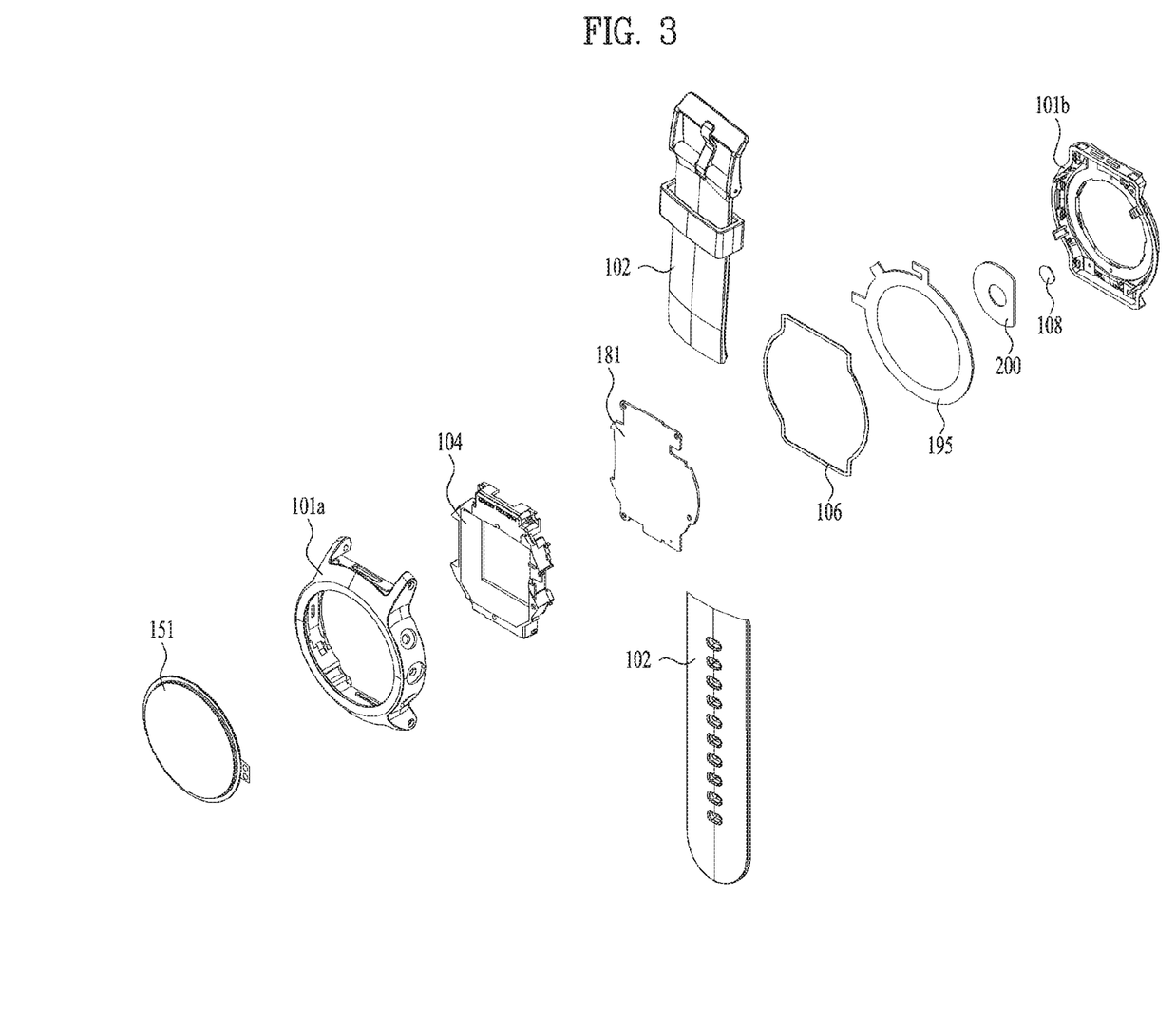
FIG. 3 is an exploded perspective diagram illustrating one embodiment of the watch type terminal.

FIG. 3 is an exploded perspective diagram illustrating one embodiment of the watch type mobile terminal 100. There are shown the display unit 151 disposed on the front surface of the body 101; a middle frame 104 loaded in the internal space formed between the front case 101a and the rear case 101b; a battery 191; a main board 181, a wireless charging coil 195; a shielding sheet 200; a magnet 108. Also, it is shown that the band 102 is connected with both sides of the body 101 to be wearable on the user's hand.

Water might flow into the hole formed in the case and configured to expose the interface unit so connect the case with the band. Accordingly, the interface exposed via the hole formed in the case may be omitted. Also, the hole formed in the case might deteriorate the exterior design, together with the problem of the water intrusion. Accordingly, it is preferred to minimize the hole formed in the case of the wearable device.

When the interface exposed outside is omitted, the data transmission or charging performed via the interface unit has to be changed in another method. Data may be exchanged with an external device by using wireless communication such as NFC or Bluetooth is used. The watch type terminal 100 may be charged by using wireless charging.

The watch type terminal 100 in accordance with the present disclosure has the display unit 151 disposed on the front surface and the battery 191 and the main board 181 may be arranged behind the display unit in order. A wireless charging coil 195 for the wireless charging may be provided in a rear surface of the main board and the rear case 1091b may be coupled to the wireless charging coil 195, while covering the main board 181. The middle frame 104 may be arranged in the rear surface of the display unit 151 and support the display unit 15 lwhile providing a loading portion configured to load diverse components.

Figure 4:
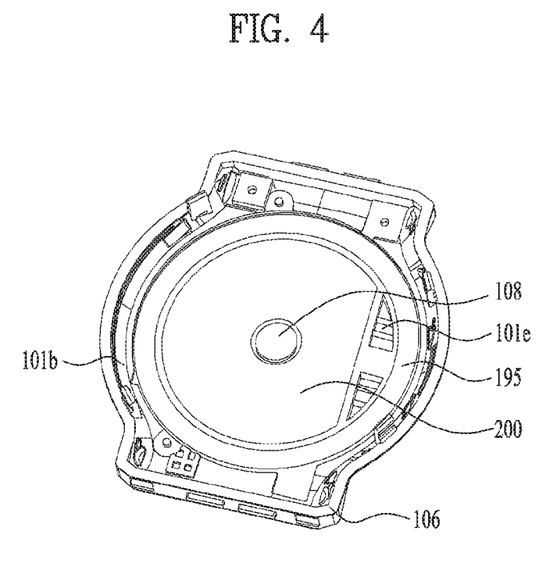
FIG. 4 is a diagram illustrating an inner surface of a rear case provided in the embodiment of the watch type terminal.

FIG. 4 is a diagram illustrating an inner surface of the rear case 101b provided in the embodiment of the watch type mobile terminal 100. It is preferred that the wireless charging coil 195 is located in an outer area of the body 101. The wireless charging coil 195 may be coupled to the inner surface of the rear case 101b to enhance wireless charging efficiency. As the wireless charging coil 195 is located in a more inner area (e.g., between the battery 191 and the main board 181), the other components might be affected more or the wireless charging function might be deteriorated more. Accordingly, it is preferred that the wireless charging coil 195 is arranged in the outermost area and coupled to the inner surface of the rear case 101b. The wireless charging coil 195 may be formed in a ring shape and a plurality of wires may be wounded in a spiral shape, while the other components are loaded in the central empty area of the ring shape.

For the strength of the rear case 101b, a rib 101e may be projected from the inner surface of the rear case 101b. The rib 101e may have a checkerboard pattern or honey-comb pattern. When the rib 101e is formed, the strength of the rear case 101b may be secured. However, the rib will occupy some space and the rib may be arranged in the wireless charging coil 195 as shown in FIG. 4 not to be overlapped with the wireless charging coil 195.

Even when coupled to the inner surface of the case of the body 101, the wireless charging coil 195 could be affected by the other components. Accordingly, a shielding sheet 200 may be further provided to concentrate the flux lines generated in a wireless charger on the wireless charging coil 195. The shielding sheet 200 may be formed of mixture of magnetic metal and polymer in a sheet shape and it may suppress the electromagnetic noise. A ferrite sheet may be used as the shielding sheet. Ferrite is a general term of a magnetic ceramic including iron oxide.

To form the Ferrite sheet, polymer paste is mixed with metallic powder having Ni, Zn, Mn, Mg and Cu and the mixture is formed in a thin sheet shape. The shielding sheet has a different permeability according to a frequency type. In case of using magnetic materials having the same property, the thickness of the shielding sheet 200 may become different according to the frequencies to absorb electromagnetic waves.

The shielding sheet 200 may be employed to enhance the wireless charging function and also minimize the effect on the user by reducing the electromagnetic radiant quantity of the watch type terminal 100. In other words, the shielding sheet 200 is meaningful in terms of safety for the electromagnetic waves.

The shielding sheet 200 has a thickness of 0.15 mm or more. When it is overlapped with the wireless charging coil 195, the shielding sheet 200 might become thicker disadvantageously. To minimize the disadvantage, the shielding sheet 200 may be arranged not to be overlapped with the wireless charging coil 195.

While it is arranged in the empty central space of the wireless charging coil 195 not to be overlapped with the wireless charging coil 195, the shielding sheet 200 may be arranged avoiding the area where the rib 101e is arranged as mentioned above.

A location relation between a transmission coil and a reception coil is important in the wireless charger using an inductive coupling method such that the structure configured to guide the watch type terminal 100 to a proper location for the wireless charging is necessary. In the embodiment, the magnet 108 may be provided as means for the guide. A pole of the magnet 108 mounted in the watch type mobile 100 is opposite to a pole of the magnet 108 loaded in the wireless charger, the watch type terminal 100 is mounted in the position in which the magnets 108 are arranged perpendicularly.

The magnet 108 shown in FIG. 4 may be arranged in the open central area of the wireless charging coil 195 and a corresponding area of the shielding sheet 200 to the magnet 108 may be omitted not to be overlapped with the magnet 108.

The embodiment shown in FIGS. 3 and 4 simply shows the structure of the rear case 101b and the arrangement of the shielding sheet 200 not to be overlapped with the magnet 108 and the wireless charging coil 195. The embodiment also has a problem of an increased thickness when the shielding sheet 200 is overlapped with the components loaded in the main board 181 disposed on the front surface of the wireless charging coil 195. Hereinafter, embodiment of the shielding sheet 210 and 220 provided not to be overlapped with the components loaded in the main board 181 will be described.

Figure 5:
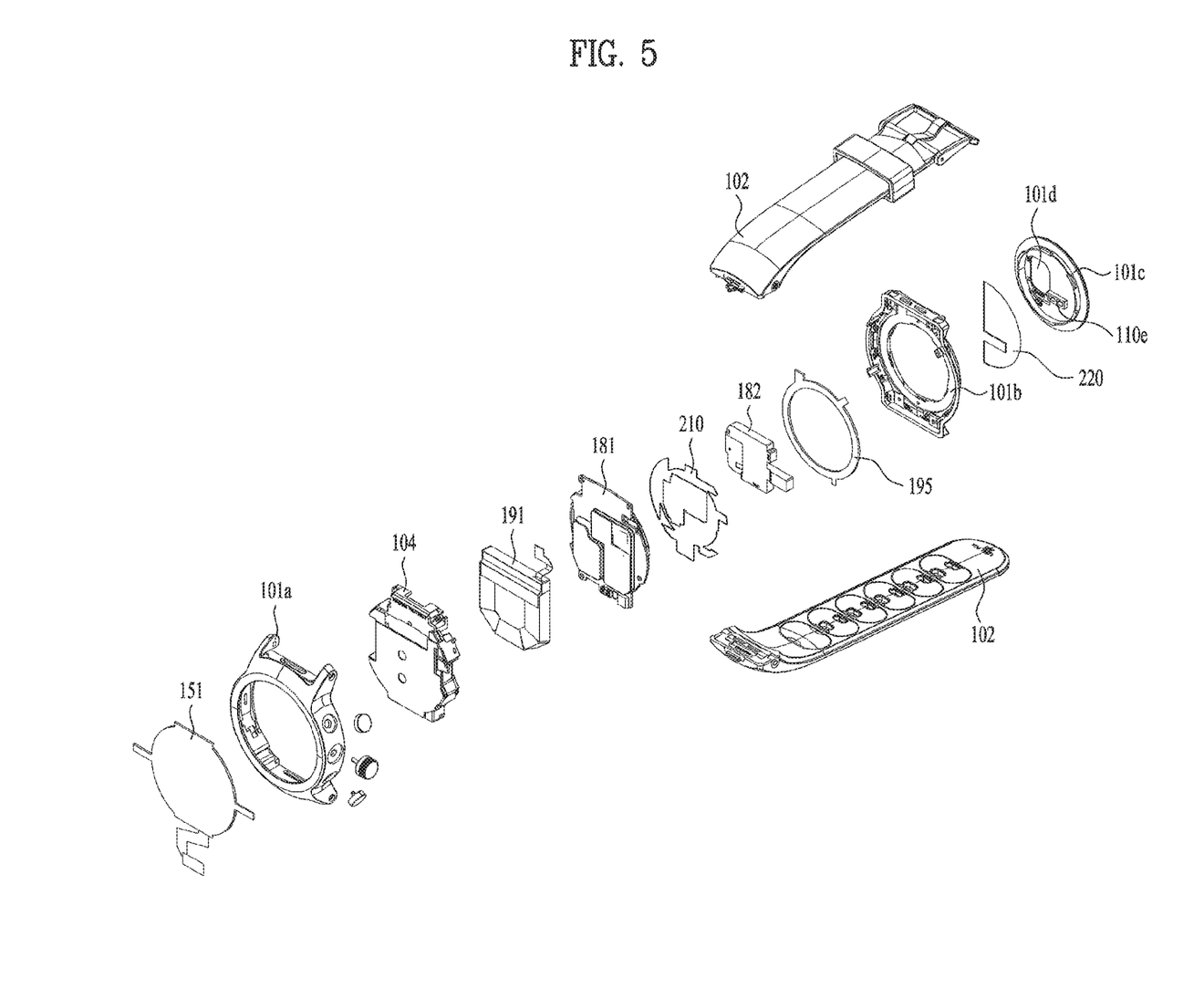
FIG. 5 is an exploded perspective diagram illustrating another embodiment of the watch type terminal.
Figure 6:
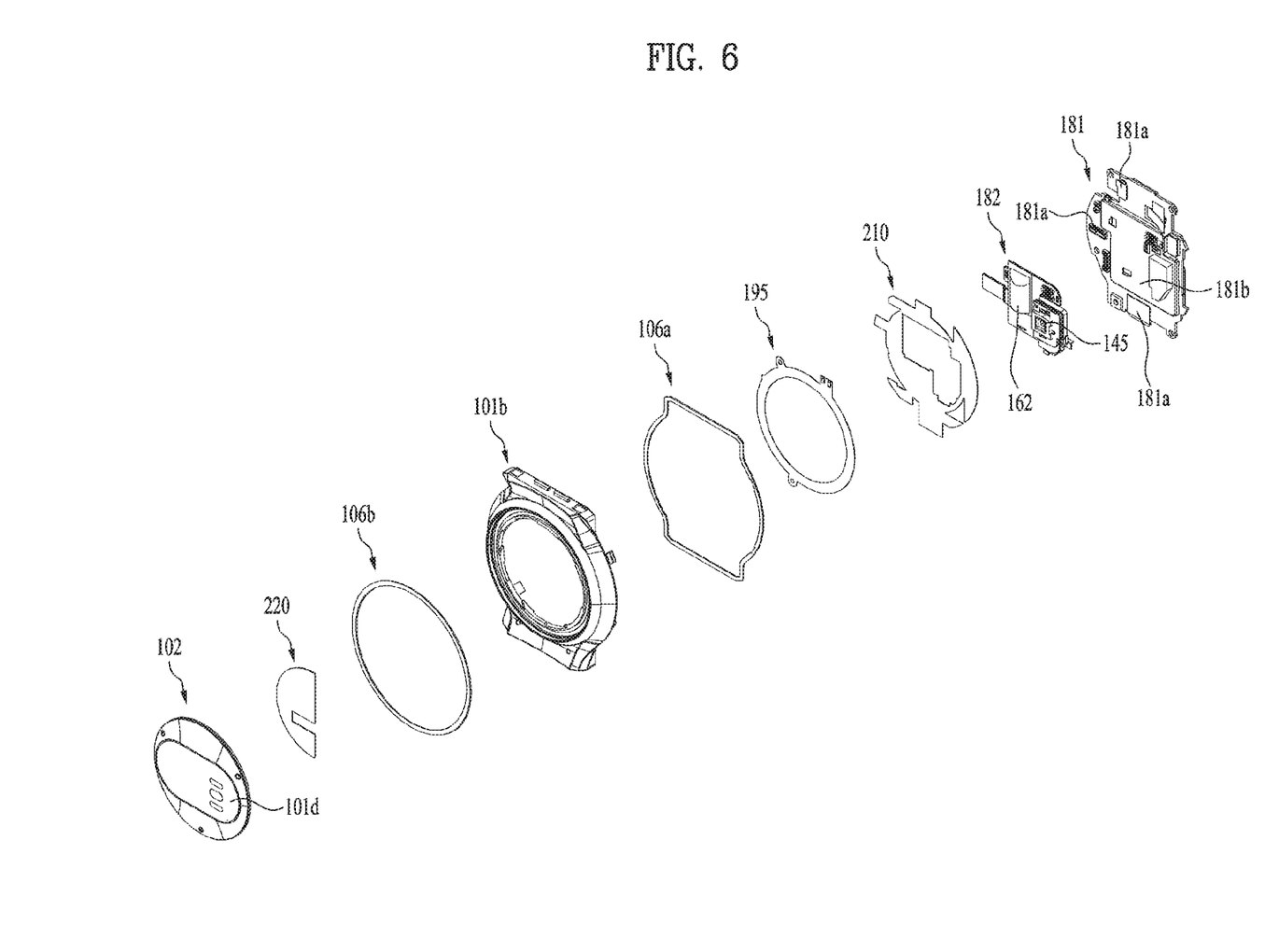
FIG. 6 is an exploded perspective diagram of a structure that is loaded in a rear surface of a main board provided in the embodiment of the watch type terminal.

FIG. 5 is an exploded perspective diagram illustrating another embodiment of the watch type mobile terminal 100 and FIG. 6 is an exploded perspective diagram of a structure that is loaded in a rear surface of a main board 181 provided in the embodiment of the watch type mobile terminal 100.

Referring to FIG. 5, the mobile terminal includes a display unit 151 including a front case 101a and a rear case 101b; a middle frame 104 provided to support the display unit 151 and secure components; a battery 191 arranged in a rear surface of the middle frame 104; and a main board 181. The watch type mobile may further include a wireless charging coil 195 provided in a rear surface of the main board 181; and a rear case 101b provided to cover internal components including the wireless charging coil 195 and the main board 181 and form a rear surface of the watch type terminal 100. Even in the embodiment, a shielding sheet 210 and 220 may be arranged near the wireless charging coil 195. This embodiment uses two shielding sheets 210 and 220 to improve the function of the shielding sheets 210 and 220.

FIG. 6 is a diagram specifically illustrating the diverse components loaded towards the rear surface of the main board 181. Different from the above-noted embodiment, a heartrate sensor 145 exposed towards the rear surface of the watch type terminal 100 and an USIM chip loading portion 162 configured to insert an USIM chip therein may be further provided in the watch type terminal. The heartrate sensor 145 has to be in close contact with the user's body and exposed to the rear surface via an opening formed in the rear case 101*b*. The USIM loading unit 162 has to be arranged near the rear case 101*b* to be inserted in the rear case 101 right after the rear case 101*b* is open.

The rear case 101*b* in accordance with the present disclosure may be divided into two parts to insert the USIM in the USIM loading unit 162 such that the watch type terminal 100 may be partially open. The rear case 101*b* may include a first rear case 101*b* coupled to the front case 101*a*, without being separated from the front case 101*a*; and a second rear case 101*b* that is separable from the first rear case 101*b* to expose the USIM loading unit 162.

A waterproof sealing 106*a* and 106*b* may be disposed between the first rear case 101*b* and the front case 101*b* and between the first rear case 101*b* and the second rear case 101*c* to prevent water from permeate there between. The waterproof sealing 106*a* and 106*b* may be formed in a ring shape to be disposed between two of the cases.

The main board 181 may be divided into a main board 181 and an auxiliary board 182 because of the limited size of the main board 181. An application processor (a) provided for a control function or a connector 181*a* connected with the components may be arranged in the main board 181. The heartrate sensor 145 or the USIM loading unit 162 arranged in the rear surface of the watch type terminal 100 may be loaded in the auxiliary board 182 and the auxiliary board 182 may be arranged in the rear surface of the main board 181.

The auxiliary board 182 may be provided for an auxiliary function of the main board 181 such that it may be formed in a smaller size than the main board 181. Accordingly, the auxiliary board 182 and the USIM loading unit 162 and the heartrate sensor 145 loaded in the auxiliary board 182 may be arranged in the open area of the wireless charging coil 195. The number of the components loaded in the auxiliary board 182 is reduced and a flexible main board 181 may be used so as to minimize the overall thickness.

To protect the diverse chips loaded in the main board 181, a shield can 181*b* may be covered as shown in FIG. 6. The display unit 151, the battery 191, the auxiliary board 182 and the connector 181*a* connected with the antenna and the touch sensor may be loaded in the main board 181. A circuit may be embedded in the main board 181 not to be exposed to a surface of the main board 181. However, the shield can 181*b* and the connector 181*a* may be projected from the surface of the main board 181.

Figure 7:
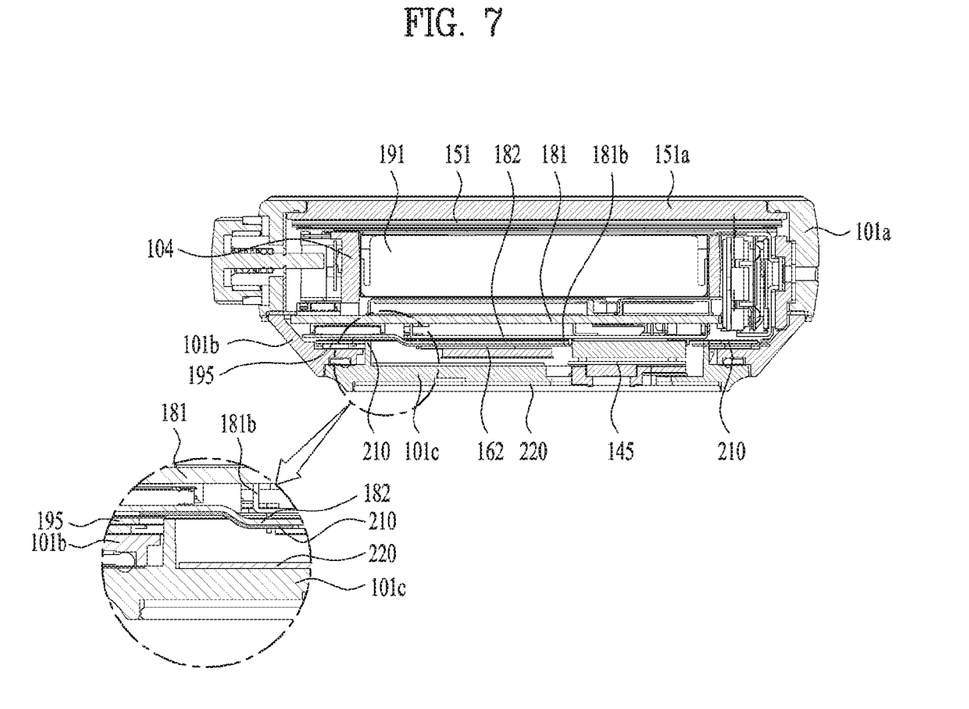
FIG. 7 is a sectional diagram partially illustrating the embodiment of watch type terminal.

FIG. 7 is a sectional diagram illustrating a state where the components shown in FIG. 5 are coupled. It is shown that the display unit 151, the middle frame 104, the battery 191, the main board 181 and the auxiliary board 182 are arranged in the internal space defined by the front case 101*a*, the rear case 101*b* and the window 151*b* from a front surface of the space (an upper area in the drawing).

The area which is projected by the shield can 181*b* and the connector 181*a* arranged in the rear surface of the main board 181 and in which the auxiliary board 182 is located may be more projected towards the rear surface. The limited space may make it difficult to arrange the wireless charging coil 195 not to be overlapped with all of the components loaded in the main board 181. However, the overlapped area between the loaded components and the wireless charging coil 195 may become thick such that the shielding sheets 210 and 220 may be cut away until not overlapped with the shielding sheets 210 and 220.

Figure 8:
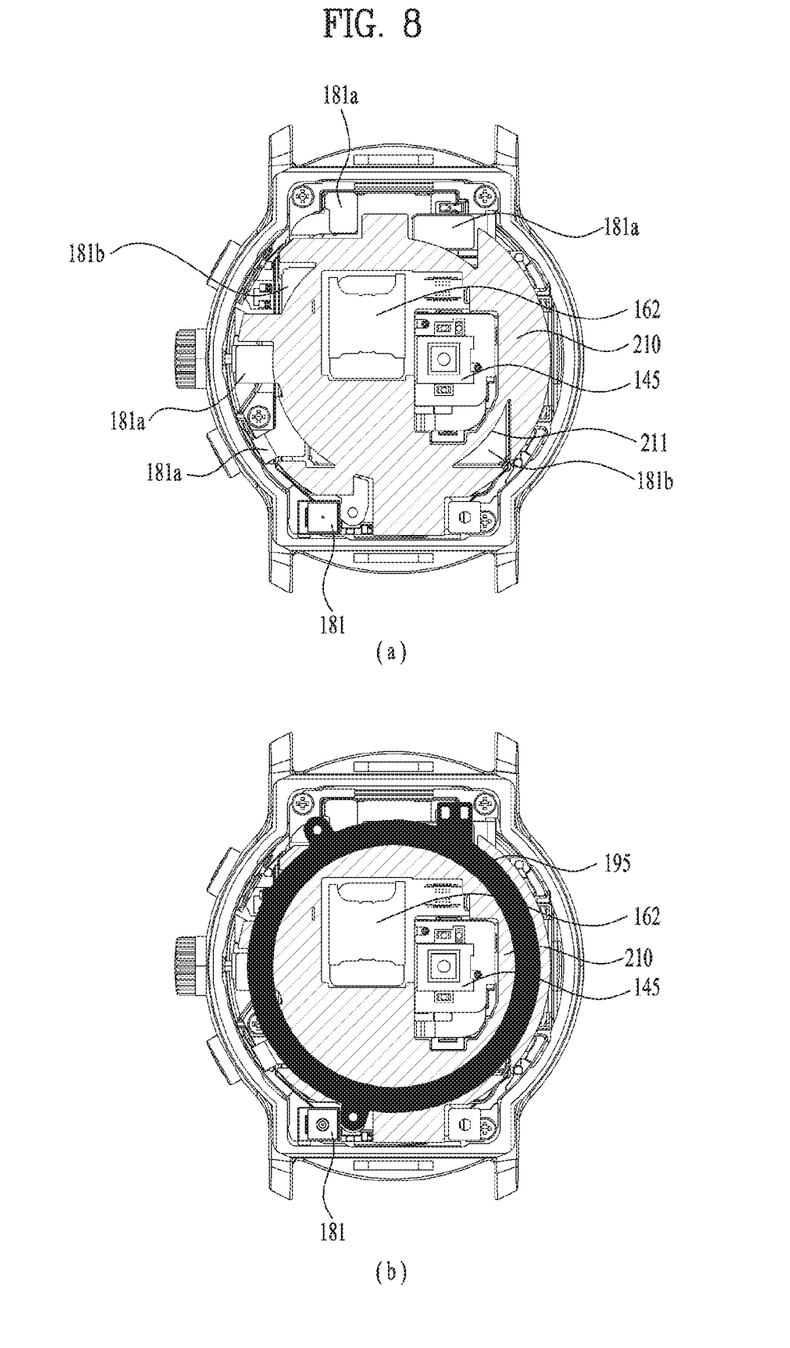
FIGS. 8 through 10 are diagrams to describe a process of disposing the shielding sheet and the wireless charging coil that are provided in the embodiment of the watch type terminal.
Figure 9:
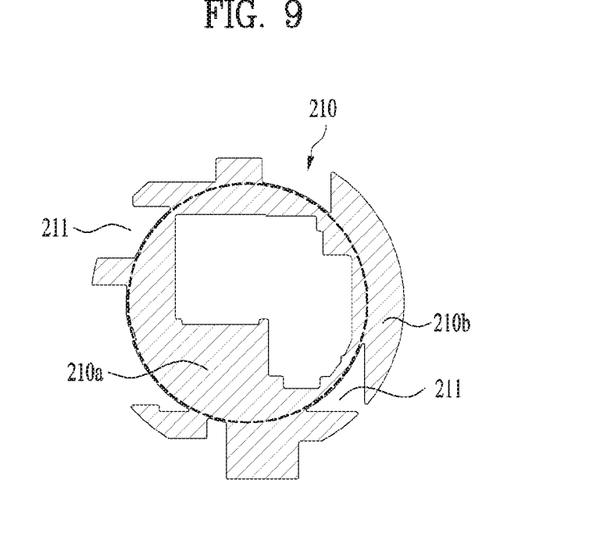
Figure 10:
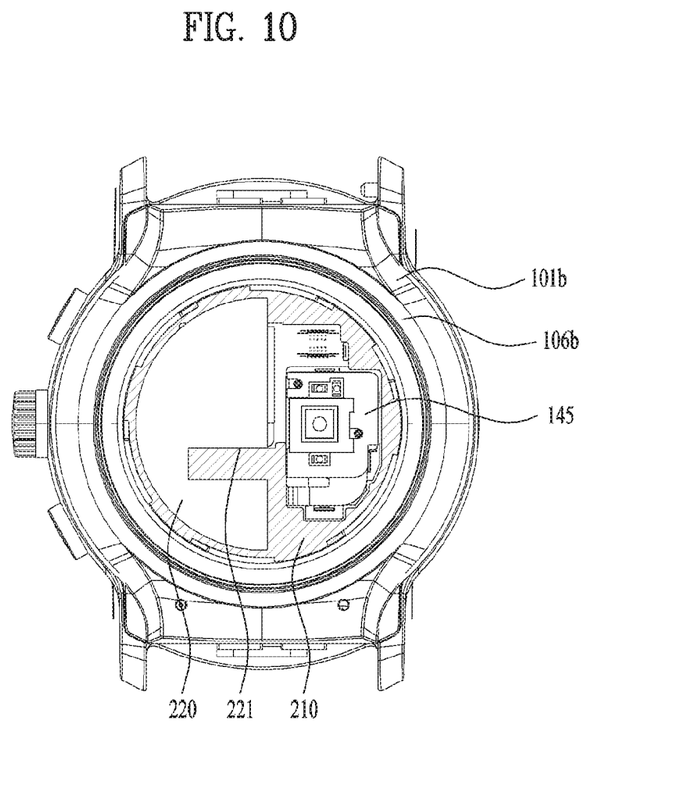

FIGS. 8 through 10 are diagrams to describe a process of disposing the shielding sheets 210 and 220 of the watch type terminal 100 and the wireless charging coil 195 that are provided in the embodiment of the watch type mobile terminal 100. FIG. 8 is a diagram to describe a state where the first shielding sheet 210 is disposed on the main board 181 and the auxiliary board 182 and a state where the wireless charging coil 195 is disposed. FIG. 9 is a diagram illustrating the first shielding sheet 210. FIG. 10 is a diagram illustrating a state where the rear case 101*b* and the second shielding sheet 200 are multilayered.

As shown in FIG. 8(*a*), the first shielding sheet 200 is disposed on the rear surfaces of the main board 181 and the auxiliary board 182. As shown in FIG. 8(*b*), the wireless charging coil 195 is disposed on the rear surface of the first shielding sheet 210.

As shown in FIG. 9, the first shielding sheet 210 includes a first shielding portion 210*a* arranged in the open area of the wireless charging coil 195; and a second shielding portion 210*b* overlapped with the wireless charging coil 195. The first shielding portion 210*a* has an open area corresponding to the heartrate sensor 145 and the USIM loading unit 162. The user is able to open the second rear case 101*c* and change USIM to insert the USIM in the USIM loading unit 162. The heartrate sensor 145 is exposed via an opening 101*d* formed in the second rear case 101*c* as shown in FIG. 8 (*a*). The opening 101*d* formed in the second rear case 101*c* may be covered with a transparent window to protect the heartrate sensor 145.

The second shielding portion 210*b* may be partially cut away (211) as shown in FIG. 8 to be omitted. The connector 181*a* and the shield can 181*b* loaded in the main board 181 are arranged in the area 211. Even the shielding sheets 210 and 220 are located in the area in which the shield can 181*b* or the connector 181*a* is overlapped with the wireless charging coil 195. Accordingly, the shielding sheets 210 and 220 may be partially omitted as shown in FIG. 8 to solve the disadvantage that the three members are multilayered. The first shielding portion 210*a* of the first shielding sheet 210 may be exposed outside when the second rear case 101*c* is open and it may coat a projection layer which might be damaged by the USIM when the USIM is loaded.

The first shielding sheet 210 has much open area such that the second shielding sheet 220 may be further attached to an inner surface of the second rear case 101*c* to reinforce the shielding function as shown in FIG. 10. The second shielding sheet 220 is attached to the second rear case 101*c*. When the second rear case 101*c* is separated, the USIM loading unit 162 may be exposed and the user is able to insert the USIM chip. The first shielding portion 210*a* could be thicker than the second shielding portion 210*b*, because the first shielding sheet 210 and the second shielding sheet 220 are overlapped with each other.

However, the heartrate sensor 145 has to be exposed via the opening 101*d*. As shown in FIG. 10, the second shielding sheet 220 has an omitted area corresponding to the heartrate sensor 145. A rib 101*e* may be projected from the second rear case 101*c* to block an entrance of the USIM loading unit 162 and prevent the inserted USIM from being released from the USIM loading unit 162. The second shielding sheet 220 may be omitted in the corresponding area 221 to the rib 101*e*.

As described above, the shielding sheets 210 and 220 provided to improve the function of the wireless charging coil 195 in the watch type terminal 100 in accordance with the embodiments of the present disclosure may be formed in the preset shape not to be overlapped with the wireless charging coil and the loaded components simultaneously. Accordingly, the body 101 may be prevented from becoming thicker.

As the present features may be embodied in several forms without departing from the characteristics thereof, it should also be understood that the above-described embodiments are not limited by any of the details of the foregoing description, unless otherwise specified, but rather should be considered broadly within its scope as defined in the appended claims, and therefore all changes and modifications that fall within the metes and bounds of the claims, or equivalents of such metes and bounds, are therefore intended to be embraced by the appended claims.

What is claimed is:

1. A watch type terminal comprising:
   a front case having a front surface in which a display unit is arranged;
   a rear case coupled to the front case from a rear area of the front case and configured to form an internal space;
   a main board provided in the internal space such that electronic components are loaded on a surface of the main board;
   a shielding sheet disposed on a rear surface of the main board; and
   a wireless charging coil provided in the internal space,
   wherein the shielding sheet has an omitted area corresponding to an overlapped area between the wireless charging coil and the loaded electronic components.

2. The watch type terminal of claim 1, wherein the electronic components comprise at least one of a shield can configured to cover a main chip or a connector.

3. The watch type terminal of claim 1, further comprising a rear surface component exposed via an opening formed in a rear surface of the rear case,
   wherein the shielding sheet has an omitted area corresponding to the rear surface component; and
   wherein the rear surface component comprises at least one of a heartrate sensor or an USIM loading unit.

4. The watch type terminal of claim 3, further comprising:
   an auxiliary board disposed on the rear surface of the main board and having the heartrate sensor loaded therein.

5. The watch type terminal of claim 1, further comprising:
   a rib projected from the rear case towards the internal space,
   wherein the shielding sheet has an omitted area corresponding to the rib.

6. The watch type terminal of claim 1, further comprising:
   a magnet loaded in the internal space,
   wherein the shielding sheet has an omitted area corresponding to the magnet.

7. The watch type terminal of claim 1, wherein the wireless charging coil is formed in a ring shape having an empty central area, and
   the shielding sheet comprises a first shielding portion arranged in the empty central area of the wireless charging coil.

8. The watch type terminal of claim 7, further comprising:
   a second shielding portion overlapped with the wireless charging coil and located between the wireless charging coil and the main board.

9. The watch type terminal of claim 8, wherein the second shielding is thinner than the first shielding portion.

10. The watch type terminal of claim 1, wherein the rear case comprises:
    a first rear case coupled to the front case;
    a second rear case detachably coupled to the first rear case; and
    a projection layer configured to cover a predetermined area of an exposed area provided in the shielding sheet when the second rear case is separated from the first rear case.

* * * * *